United States Patent [19]
Chadwick

[11] Patent Number: 6,063,314
[45] Date of Patent: May 16, 2000

[54] METHOD FOR ACCURATE REPLICATION OF SHAPED ARTICLES USING SINTERABLE POWDERS

[75] Inventor: Thomas Chadwick, Nipomo, Calif.

[73] Assignee: Den-Mat Corporation, Santa Maria, Calif.

[21] Appl. No.: 09/082,545

[22] Filed: May 21, 1998

[51] Int. Cl.[7] .............................. A61C 13/00; C04B 33/28
[52] U.S. Cl. .................. 264/16; 264/17; 264/19; 264/651; 264/86; 264/219; 264/222; 264/226; 264/227; 419/38; 419/39; 419/40; 419/66
[58] Field of Search .................... 264/16, 17, 19, 264/651, 86, 219, 222, 226, 227; 419/38, 39, 40, 66

[56] References Cited

U.S. PATENT DOCUMENTS 5,852,248  12/1999  Chadwick ........................ 419/2
5,852,766  12/1999  Chadwick et al. .

*Primary Examiner*—James Derrington
*Attorney, Agent, or Firm*—Dorsey & Whitney

[57] ABSTRACT

Shaped article replicas which are proportionately accurate replicas of a shaped article and which are equal, greater or smaller in size than said shaped article are made by preparing a swellable polymer replica of said shaped article; immersing said swellable polymer replica in a swelling agent system under conditions which will enlarge said polymer replica to a predetermined extent; forming a casting mold of such enlarged polymer replica; making a powder compact in said casting mold and heating said powder compact to produced a proportionately accurate solid replica of a predetermined size.

27 Claims, 1 Drawing Sheet

METHOD FOR ACCURATE REPLICATION OF SHAPED ARTICLES USING SINTERABLE POWDERS

FIELD OF THE INVENTION

This invention relates generally to the fabrication of dimensionally and/or proportionately accurate replicas of shaped articles, especially articles having complex shapes, using sinterable powders such as ceramic powder, metal powder, plastic beads or carbon powder.

BACKGROUND OF THE INVENTION

The fabrication of ceramic, metal and other shaped articles by sintering powder compacts, whether formed by die pressing, slip casting, or injection molding, involves a series of certain basic steps. The raw sinterable powder, such as ceramic or metal powder is first mixed with a binder and sometimes a suitable solvent. The binder-powder mixture is then formed or shaped and any solvent, if present, is removed. In the final step the powder compact is heated under conditions which lead to elimination of the binder material and any solvent that may still have been present. Continued heating results in the consolidation of the individual grains of the sinterable powder, such as ceramic, plastic or metal powder and the creation of a solid monolithic object that is free of voids.

Although processes such as die pressing, slip casting, and injection molding are capable of delivering finished objects of great complexity in a bewildering array of materials, they all suffer from one major drawback. These processes all involve forming compacted powders into complex shapes. Powder compacts of these materials invariably have numerous voids between the individual constituent powder grains of the compacted powder. Typically such compacted powder objects contain only from about 40% to 65% solids, by volume, before heating. Voids amounting to 35% to 60% constitute the remainder. When such compacts are heated, the voids are eliminated, and the powder compact undergoes linear shrinkage on the order of 15%–25%.

When an accurate replica of a shaped article is sought in terms of either or both size and proportional configuration, it is necessary to oversize the powder compact to an extent sufficient to offset the shrinkage which occurs during the heating of the powder compact, which is the last step of the procedure.

By way of illustration, if a precise dimensional replica of a shaped article is desired when using an injection molding process, the injection mold die cavities must be enlarged by an amount equal to the amount of shrinkage that will take place when the molded powder is heated. The same type of enlargement must be made to compensate for shrinkage on heating in all powder forming processes.

The dimensional compensation needed for accurate replica of shaped articles can be provided by hand enlargement of a mold, produced from the article to be replicated. However, this solution to the problem is obviously labor intensive and requires great skill to produce a proportionately accurate oversized mold. Since the careful crafting of the oversized molds is obviously time consuming and costly, the use of this technique is usually limited, either to replicas where the high cost of the finished article is not a deterrent or to the production of large numbers of identically shaped articles. These are to be distinguished from manufacturing situations where only a few relatively low valued replicas are to be made. In addition to being highly labor intensive, the accuracy of sculpting to provide shrinkage compensation for complex objects is completely dependent upon the skill of the artisan. As observed by Randall German in the book "Powder Injection Molding", p.255, tool design can involve using the ". . . costly trial-and-error approach."

The problem of shrinkage resulting from heating can be avoided, in some instances if it is acceptable for the replicated article to be produced from materials that exhibit only a slight amount of shrinkage. For example molten metals or glass can be cast in a mold with very little resulting shrinkage, but there are only a very limited number of circumstances where these materials are acceptable for the final replicated article. There also have been attempts to develop special ceramics which undergo a phase change and some degree of expansion during heating to thereby counteract the volume contraction which would otherwise result from the elimination of voids. Unfortunately these materials have found only limited use, because other essential properties of the final product, such as thermal expansion, strength, fracture toughness, etc. are not adequate for most applications.

DESCRIPTION OF THE PRIOR ART

Replicating shaped articles by molding a sinterable powder into the shape of the article to be replicated followed by heating at high temperature to produce strength and structural integrity is a technique that has been known for centuries. See for example F. H. Norton, "Fine Ceramics—Technology and Applications" Robert E. Kreiger Publishing Co., Malaba, Fla., 1987, pp. 101–129; "Slip-casting of Non-clay Materials" Rado, P. Trans. J. Brit. Ceramic Soc., 72 (7), 291–297 (1973) and "Properties of Slip-Cast Transformation-Toughened Beta"—$Al_2O_3/ZrO_2$ Composites" D. J. Green and M. G. Metcalf Am. Ceram. Soc. Bull., 63 [6] 803–820 (1984).

Artists often wish to produce enlarged versions of works of art. Pantographs are commonly used for enlarging two-dimensional works of art. Very complex three-dimensional pantographs for producing enlarged replicas of three-dimensional works have also been developed but these are strictly mechanical approaches to the creation of enlarged shaped articles. While these methods may be acceptable for producing molds for the production of large volume items, such as toys, where precise replica is not essential, they do not have sufficient accuracy for the production of replicas where accuracy is essential such as for the production of dental onlays and inlays.

SUMMARY OF THE INVENTION

It has now been found that a variety of different polymers can be made to swell to a precise predetermined degree and without dissolving, by immersion in a properly formulated swelling agent system.

Dimensionally accurate replicas of shaped articles, using any of the conventional sinterable powders in a powder sintering process, can be accomplished easily by a simple technique. This procedure involves the selection of a swellable polymer which can made to increase in size in a reproducible manner and to a pre-selected extent, by immersion in an appropriate swelling agent system. The ability to tailor a swelling agent system and polymer to expand the polymer to essentially the same extent as the shrinkage resulting from the heating of the sinterable powder selected for the replica, allows the fabrication of one or even large numbers of dimensionally accurate replicas of shaped articles, without the necessity for time consuming and costly hand labor. This ability also makes it possible to produce replicas that are greater or smaller in size than the original to a predetermined extent and yet remain proportionately accurate in relation to the original.

Thus, in accordance with this invention, if it is desired to produce a solid and dimensionally accurate replica of a shaped article, a replica of said shaped article is first formed from a swellable polymer. The swellable polymer is then immersed in a swelling agent system at a temperature and for a time sufficient to uniformly swell said swellable polymer to a predetermined extent. A cast is then prepared of the polymer replica and a sinterable powder compact, such as ceramic powder, is formed in said casting mold. The cast may be formed from any suitable substance, such as Plaster of Paris. Finally, the sinterable powder compact is heated in a selected atmosphere for a predetermined time or times at one or more predetermined temperatures. The enlargement of the oversized compact casting exactly compensates for the shrinkage that occurs on heating, resulting in a dimensionally accurate replica of the original article, with little or no hand labor.

The invention also lends itself to the production of proportionately accurate replicas of shaped articles which are either larger or smaller in size than the original shaped article. This can easily be accomplished by following the procedure described above with only slight modifications. For example, a proportionately accurate larger replica of a shaped article can be produced, employing the above described procedure, by using a swellable polymer and swelling agent system which has the ability to swell the polymer to a specific greater extent than the degree of shrinkage which will result from the heating of the sinterable powder selected for the solid replica. Conversely, a proportionately accurate smaller replica of a given size can be produced by selecting a swellable polymer which can be made to swell only to a predetermined extent which is less than the shrinkage which occurs when the powder compact is heated. Obviously, the procedure for producing such larger or smaller replicas can be repeated a number of times if necessary to produce replicas of the desired size.

DETAILED DESCRIPTION OF THE INVENTION

I. THE SINTERABLE MATERIAL

Figure 1:
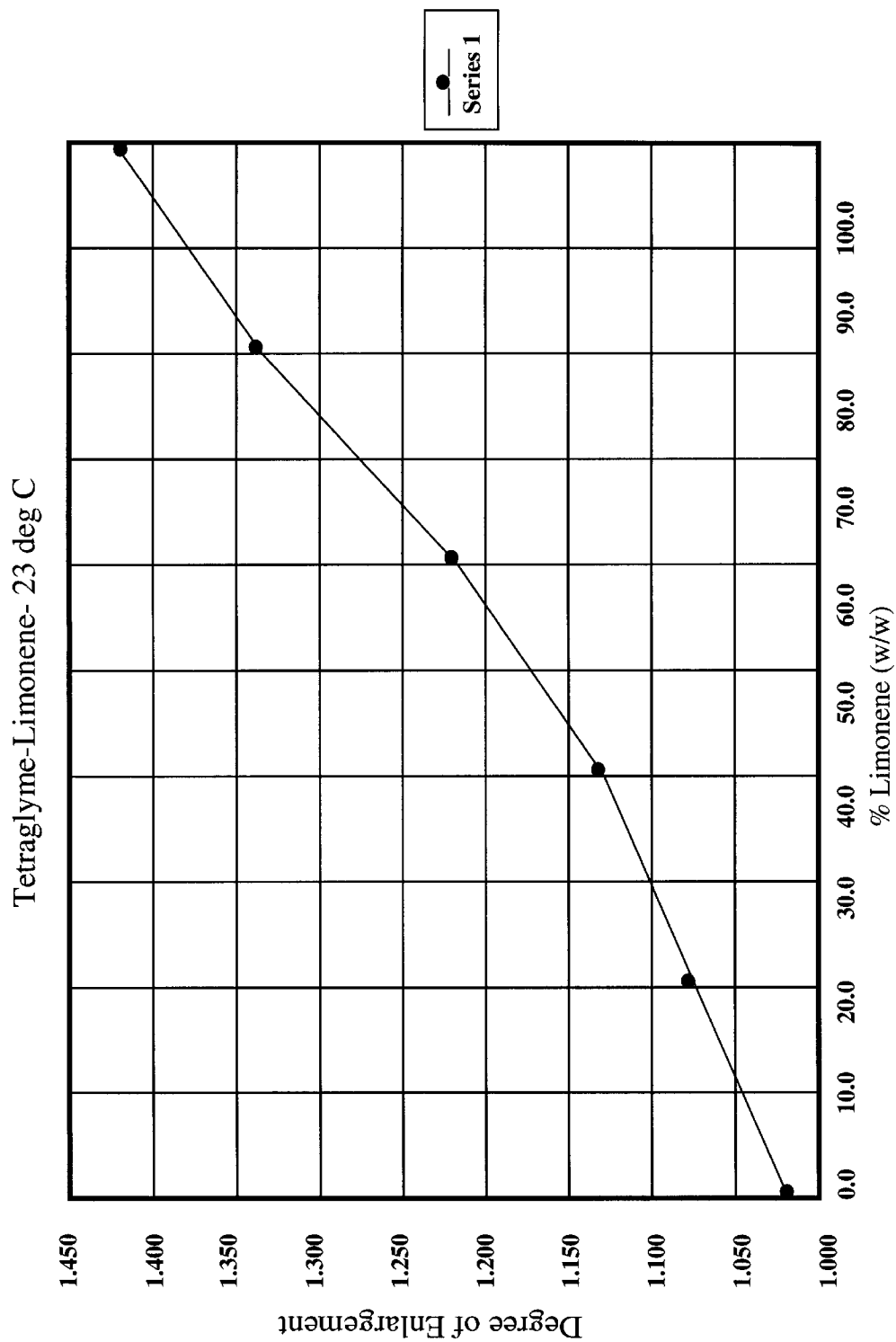
FIG. 1 is a graphical representation of the swelling ratios of a certain RTV silicone elastomer when immersed in swelling agents comprised of mixtures of tetraglyme and limonene in various concentrations.

This invention is ideally suited to the accurate reproduction of shaped articles from a variety of different sinterable materials. While the method of this invention can be used to replicate many different kinds of shaped articles, such as works of art; it is especially suited to the production of dental restorations in the form of dental onlays and inlays.

The first step in the practice of this invention is the selection of the sinterable powder to be used for production of the desired solid replica. This step is followed by a determination of the precise amount of shrinkage that will occur when the selected sinterable material is fired under specific conditions in accordance with a specific heating schedule. This shrinkage factor is hereinafter referred to as the "coefficient of shrinkage."

The shrinkage, which will take place upon heating a powder compact of a sinterable substance, will be influenced primarily by the following factors:

a) the particle size(s) of the sinterable powder
b) the degree of packing (bulk density) of the sinterable powder
a) the time, duration and temperature at which the powder compact (molded sinterable powder) is heated and
a) the chemical composition and constituents of the sinterable powder.

The accuracy of the determination of the coefficient of shrinkage plays a major role in determining the dimensional and proportional accuracy of the final solid replica.

Any sinterable powder can be used in the practice of this invention. Among the sinterable powders that are useful are: clay and clay containing ceramics, alumina, fused silica, beryllia, urania, calcia, magnesia, spinel, calcium fluoride, magnesium fluoride, titanium nitride, zirconium boride, silicon carbide, titanium carbide and cermets as well as metal powders, such as gold, silver, bronze, zinc, tungsten, molybdenum, stainless steel, titanium, chromium, silicon as well as metal alloys and even non-metals such as wood and graphite. Metal Powders are generally preferred. For dental restorations the preferred materials are ceramics, especially zirconium oxide or zirconia. The literature is replete with disclosures of the wide variety of available sinterable materials and methods for casting them into cast articles. See for example, P. Rado, "Slip-Casting of Non-clay Materials," *British Ceramic Society, Transactions and Journal,* 72(7), 291–297 (1973). The selection of the sinterable material to be employed for the slip casting of the final product is dictated almost entirely by the physical properties and appearance desired in the final product. The fundamental techniques employed in the heating of the final slip casting or powder compact (these terms are used interchangeably herein) date back to biblical times and are well documented in the literature. The only requirement of the sinterable powder used in the practice of this invention is that after production and heating of the powder compact in the same manner as was employed in determining its coefficient of shrinkage, the final casting will have the desired physical and dimensional properties.

The amount of shrinkage that will occur upon the heating of any given sinterable powder is preferably determined experimentally, to permit accurate measurement and comparison of the dimensions of the powder compact (molded sinterable powder) relative to the dimensions of the final solid sintered casting. When establishing the coefficient of shrinkage for a given sinterable system each of the factors listed above for the determination of the coefficient of shrinkage must be noted carefully so that the result obtained can be reproduced accurately.

In accordance with conventional slip casting procedures the sinterable powder is mixed with a suitable liquid which can be water or an organic liquid and then packed into a preferably porous mold. After the liquid has evaporated or migrated into the mold, the powder compact, or slip casting, is removed and fired to produce the desired solid article. The amount of liquid employed is a factor that must be taken into account along with other factors in determining the coefficient of shrinkage of the sinterable composition. Of particular importance is the size of the sinterable powder particles, which establish the bulk density or packing density of the powder compact. It is important to avoid the use of packing densities that are too low which can result in warping or other dimensional distortions when the slip casting is fired.

II. THE SWELLABLE POLYMER

Any polymer that is capable of being swelled in an essentially uniform manner and to a reproducible extent can be used in the practice of this invention, provided the polymer is insoluble in the swelling agent system selected for swelling the polymer and provided also that after immersion in the swelling agent, the swelled polymer retains sufficient structural integrity to permit its use in the molding procedures employed in the practice of this invention. The ratio of the dimensions of an unswollen polymer to the same polymer, after immersion in a specified swelling agent system at a given temperature for a specific period of time, is hereinafter referred to as the "coefficient of expansion."

A wide variety of different polymers are capable of use in the practice of this invention. The most readily available polymers that are capable of being reproducibly swelled, without dissolving, are elastomeric polymers and cross-linked polymers. Among the useful polymers having the properties desired for accurate dimensional slip casting are elastomers, as for example: silicone elastomers, polyurethane elastomers, vulcanized natural latex, polysulfide elastomers and polyether elastomers. Other examples of useful swellable polymers are thermoplastic polyurethanes, styrene/butadiene/styrene block copolymers, styrene/ethylene-butylene/styrene block copolymers, polyether/polyamide copolymers, ionic polymers and a variety of plastic/rubber alloys. These polymeric materials are well known and are readily available from a multitude of commercial suppliers. The preferred swellable polymers useful according to this invention are elastomers, more preferably silicone elastomers, and most preferably an RTV silicone elastomer.

III. THE SWELLING AGENT SYSTEM

Virtually any organic liquid can be used in the practice of this invention, provided that it is essentially non-reactive with the swellable polymer selected for use in accordance with the invention and provided also that it does not dissolve the swellable polymer. Mixtures of various swelling agents are particularly useful due to the possibility of adjusting the ratio of a plurality of different swelling agents having different swelling effects on the swellable polymer so as to obtain a specific desired ratio between the coefficient of expansion and the coefficient of shrinkage of the sinterable material selected.

If the swellable polymer selected is a hydrophilic polymer, water as well as aqueous solutions of salts and other substances such as alcohols and esters, which are miscible in water, can also be used as the swelling agent system employed in the practice of this invention.

The extremely wide range of possible swelling agent systems that are capable of use in accordance with invention allows the selection of the swelling agent system to be largely a matter of choice. Considerations such as cost, flammability and waste disposability may therefore represent the most important factors in the selection due to the fact that there are many different swelling agent systems that can be used to achieve the desired coefficient of expansion. Because the temperature and the duration of the immersion of the selected polymer all have an influence of the degree of swelling of the polymer, it is necessary to determine the coefficient of expansion by experimentation, if accurate dimensional and/or proportional replica is to be achieved. The procedure for making this determination is quite simple:

1. A cylindrical casting of the polymer selected for use is cut into discs of uniform thickness.

2. The individual discs are then immersed in a representative variety of different swelling agent candidates maintained at a desired temperature.

3. The specimen discs are periodically removed and measured to establish the degree of swelling of the individual discs over time to thereby establish the coefficient of expansion for the various swelling agent systems employed in the experiment.

The thickness measurements will establish a profile of the length of time needed for the selected swelling agent to fully permeate the specimen discs. This will provide an indication of the time required to achieve essentially maximum or near maximum expansion of the selected swellable polymer in a reproducible manner. Normally this is a period of time is on the order of 8 to 128 hours at room temperature.

An important feature of this invention resides in the use of combinations of swelling agents that can used to produce a ratio of swelling which is different from that of individual pure swelling agents. This is important because it is very unlikely that any single pure swelling agent will provide a degree of swelling which will provide the precise ratio of swelling needed to compensate for the coefficient of shrinkage of the selected sinterable composition or to provide a final solid product of the desired size. The use of such swelling agent mixtures permits the adjustment of the coefficient of expansion of the selected swellable polymer to very precisely compensate for the coefficient of shrinkage of the sinterable material selected. The ideal swelling agent combinations that allow for such precise adjustment are mixtures of a swelling agent that has little or no ability to cause the selected polymer to swell, such as tetraglyme, with another swelling agent that has a considerable ability to cause the selected polymer to swell, such as limonene. By testing a series of mixtures of such combinations and plotting a curve of the results obtained in graphical form, a very satisfactory curve can be produced which will allow the selection, by interpolation, of a swelling agent mixture for the selected polymer which will very precisely compensate for the coefficient of shrinkage of the selected sinterable composition. FIG. 1 was drawn from data produced in Example 1 below and illustrates such a curve.

FIG. 1 is a graphical representation of the determination of the coefficient of swelling of an RTV silicone elastomer (Quick Pour Duplicating Material, a product of Ceramco, Inc., Burlington, N.J.) determined by the method described above, by immersion in mixtures of tetraglyme and limonene in the various ratios indicated, at a temperature of 23 degrees centigrade for a period of 26 hours. These experiments demonstrate the ease of selecting a swellable polymer and protocol using various swelling agent systems which are capable of providing coefficients of swelling extending over a range of about 1.0 to 1.42.

The following is a listing of pure swelling agents ranked in the order of their power to cause swelling of a RTV silicone polymer:

| Pure swelling agent | Thickness Ratio after immersion |
|---|---|
| limonene | 1.51 |
| turpentine | 1.49 |
| mineral spirits | 1.42 |
| dichloromethane | 1.42 |
| toluene | 1.42 |
| ethyl acetate | 1.41 |
| 2-butanone | 1.24 |
| acetone | 1.10 |
| 2-methoxy ether | 1.08 |
| sulfolane | 1.04 |

-continued

| Pure swelling agent | Thickness Ratio after immersion |
| --- | --- |
| N,N-dimethylformamide | 1.03 |
| dimethylsulfoxide | 1.03 |
| furfuraldehyde | 1.03 |
| triglyme | 1.02 |
| tetraglyme | 1.01 |

Mixtures of the swelling agent materials are especially useful as they make it possible to achieve a variety of different coefficients of expansion, by employing mixtures of different swelling agents with a selected swellable polymer. This makes it possible to achieve a more accurate balance between the coefficient of expansion of the polymer selected and the coefficient of shrinkage of the sinterable powder composition selected for the replica.

An important factor in the selection of the swelling agent system to be used in accordance with the process is the rate at which swelling agent evaporates from the swelled polymer casting. This property is determinative of the time allowed for producing a mold of the swelled specimen before swelling agent evaporation begins to cause shrinkage of the polymer back to its original size. Swelling agents which evaporate rapidly, such as dichloromethane and toluene are less favored because their rapid rate of evaporation reduces the amount of time available for producing the slip casting cavity mold.

To ensure a high level of accuracy in the production of a shaped article replica it is preferred to make a determination of the coefficient of expansion for each individual batch of swellable polymer selected, due to possible variations in the coefficient of expansion resulting from differences which can occur due to subtle batch to batch variations.

IV. THE PROCEDURE

Accurate replication of a complex shaped article can be accomplished in accordance with this invention by following the procedural steps set forth below:

1. Select the sinterable composition that is to be used for casting the desired solid replica.

2. Determine the heating schedule and other conditions that are to be used in heating a powder compact of the sinterable composition to produce the solid replica.

3. Prepare a test piece of the selected sinterable composition and take measurements before and after heating in accordance with the heating schedule and conditions to be used in the final step to thereby determine the coefficient of shrinkage for the sinterable composition using the selected heating protocol.

4. Select a swellable polymer and swelling agent system and conditions, such that the polymer and swelling protocol will result in a coefficient of expansion that essentially compensates for the shrinkage of the sinterable composition selected in step 2 above, when heated. To achieve such equivalence, the coefficient of expansion for the selected polymer should be equal to 1 divided by the coefficient of shrinkage of the sinterable selected for use in step 1 above. In other words the mathematical relationship between these two measures should satisfy the following equation:

Coefficient of Expansion=1/Coefficient of Shrinkage

This step may require a minor amount of experimentation to empirically define the swelling agent system, temperature and duration of immersion needed to obtain the desired coefficient of swelling.

If, however it is intended that the final replica be larger or smaller than the original, this can easily be accomplished by selecting a swellable polymer exhibiting a coefficient of expansion having the desired ratio relative to the coefficient of shrinkage of the selected sinterable powder composition. Thus, for example a 1.1:1 enlargement can be achieved by using a swellable polymer having a 1.4375 coefficient of expansion in conjunction with a sinterable powder composition having a 0.8 coefficient of shrinkage. A ten percent reduction in the size of the original can be accomplished, for example, by employing a swellable polymer having a coefficient of expansion in conjunction with a sinterable powder composition having coefficient of shrinkage equal to 0.8. Whether the replica product is smaller or larger than the original shaped article, the replica product produced by the method of this invention remains proportionately accurate in relation to the original shaped article.

5. Produce a mold of Plaster of Paris, epoxy resin or another suitable material, using the shaped article to be replicated or a model thereof.

6. Produce a casting from the mold using the selected swellable polymer.

7. Immerse the swellable polymer casting in the selected swelling agent system in accordance with the swelling protocol selected in step 4 above for a sufficient period of time to ensure essentially complete penetration of the swelling agent system throughout the polymer casting.

8. Produce a further slip casting mold from the swelled polymer material using Plaster of Paris or other suitable material.

9. Produce a powder compact in the mold produced in step 8 using the sinterable composition selected in step 1.

10. After drying, remove the powder compact from the mold and subject it to heating in accordance with the heating protocol used in establishing the coefficient of shrinkage for the selected sinterable composition.

V. EXAMPLES

Example 1

Determination of the Coefficient of Swelling of the Swellable Polymer

Cylindrical samples of an addition curable vinyl polydimethylsiloxane RTV elastomer (Quick Pour Duplicating Material sold by Ceramco Inc., Burlington, N.J.) were prepared by mixing equal weights of the catalyst and silicone base material. The thoroughly mixed blend was poured into a cylindrical mold cavity (12.1 mm Diameter by 60 mm Length). The polymer contained in the cylinder was allowed to cure for approximately thirty minutes and was then removed from the cylinder cavity using a die plunger and arbor press. 6–8 mm Thickness samples were sliced from the solidified polymer samples using a razor blade. The finished specimens were all right cylinders measuring 12.07 mm in diameter and ranging from 6 to 8 mm in thickness. The specimens were allowed to cure for a period of 24 hours before proceeding to the next step.

Mixtures of limonene and tetraglyme swelling agents were prepared gravimetrically from the pure swelling agents and placed in high density polyethylene containers with screw closures. The range of swelling agent samples prepared included pure limonene, pure tetraglyme and mixtures of 20%, 40%, 60% and 80% tetraglyme, the remainder being limonene. Two cylindrical samples of polymer were placed in each of the containers and allowed to equilibrate at 23° C.±2° C. for 24 hours.

The samples were removed from the container and blotted dry with a tissue. The diameter of each specimen sample was measured with an electronic caliper by slowly opening the jaws of the caliper until the sample fell free of the caliper by its own weight. This measurement was repeated for each of the specimen samples that had been immersed in swelling agent as well as a standard unswollen polymer sample. The diameters of the two samples immersed in each of the different swelling agents and swelling agent mixtures were averaged and the coefficient of swelling resulting from immersion in each of the different swelling agent compositions calculated by determining the ratio of the diameter of the swelled specimen to that of the unswollen standard.

The following results for various mixtures of tetraglyme and limonene were obtained by these procedures:

| Tetraglyme/Limonene Swelling Agent Mixtures | | |
|---|---|---|
| % Tetraglyme | % Limonene | Swelling Ratio |
| 0.0 | 100.0 | 1.425 |
| 20.0 | 80.0 | 1.330 |
| 40.0 | 60.0 | 1.218 |
| 60.0 | 40.0 | 1.130 |
| 80.0 | 20.0 | 1.067 |
| 100.0 | 0.0 | 1.012 |

The values obtained for tetraglyme systems were plotted as shown in FIG. 1. FIG. 1 is a graphical representation of the coefficients of swelling set forth above. This graphical representation of the tetraglyme/limonene system makes it possible to interpolate between the measured values to obtain a swelling agent system which will provide any desired coefficient of swelling falling within the overall range. Thus, if for example a swelling system having a 1.35 coefficient of expansion is needed, interpolation based on FIG. 1, shows that a mixture of 84 percent limonene and 16 percent tetraglyme will provide the desired coefficient.

Example 2

Determining the Coefficient of Shrinkage

A slip mixture of zirconium oxide and water was prepared from 16.00 g zirconium oxide powder (TOSOH Zirconia TZ-3YS powder) and 4.00 g distilled water. After thorough mixing with a plastic spatula, the mixture was allowed to stand for 5 minutes to allow air bubbles to escape. Two castings were made in a series of Plaster of Paris cavity molds of dental onlays of different sizes. The castings were made by rapidly filling the cavity molds with the slip mixture using a disposable plastic pipette. The castings were allowed to stand for approximately 5 seconds (this allowed the wall thickness of the cast piece to reach a satisfactory level), after which time any excess slip mixture was removed. Castings of rectangular plates were made in rectangular molds measuring 30 mm by 34 mm by 6 mm. In all cases the resultant castings were left in the mold for approximately ten minutes prior to re4moval. The unfired zirconia castings were placed on an alumina insulation blocks and allowed to air dry for approximately 12 hours.

The unfired zirconia castings, supported on alumina insulation blocks, were placed in a high temperature furnace (Thermolyne High Temperature Furnace maximum temperature 1700 C.) and fired in an air atmosphere. The heating schedule was as follows:

1. Heat to 500° C., increasing temperature at a rate of 1° C. per minute with no hold at 500° C.

2. Heat from 500° C. to 1500° C. increasing temperature at a rate of 2° C. per minute with a 2 hour hold at 1500° C.

3. Cool to room temperature at a temperature reduction rate of 4° C. per minute.

After the fired castings had cooled, their length and breadth was carefully measured and the ratio of the size of the casting to the original model determined. From these measurements it was determined that:

1. The coefficient of shrinkage of the zirconia ceramic slip mixture was 0.773 plus or minus 0.009 based on 6 replicas.

2. The selected RTV composition when immersed in a swelling agent mixture comprised of 27.4% tetraglyme and 72.6% limonene for a period of 8 hours will provide a coefficient of swelling that will equal the coefficient of shrinkage of the selected ceramic zirconia slip composition.

This ratio was determined by reference to a graph of the swelling ratio plotted as a function of the swelling agent composition in accordance with the procedure disclosed in Example 1, above.

Example 3

Preparation of Slip Casting Mold

A dental onlay for a molar tooth was selected as the model of the shaped article to be replicated in this example according to the invention. An RTV models of the onlay were prepared by casting an equal weight mixture of the catalyst and base components of the selected silicone elastomer composition (Quick Pour Duplicating Material, a product of Ceramco, Inc. of Burlington N.J. which was the material used in determining the coefficient of swelling in Example 1), in a cavity mold produced directly from the onlay. The RTV models of the onlay were allowed to cure for approximately 10 minutes and were then removed and allowed to cure for an additional 24 hours.

Example 4

Swelling the RTV Models

The RTV models prepared in Example 4 were immersed in mixtures of 20%–80% (w/w), 27.4%–72.6% (w/w), 30%–70% (w/w), 40%–60% (w/w) and 60%–40% (w/w) percent tetraglyme and limonene and allowed to stand for a 24 hour period at a temperature of 23°±2° C. The swollen models were then removed and blotted dry.

Example 5

Preparing the Casting Mold

A mixture comprised of 100 g of Plaster of Paris and 50 g of distilled water was prepared and placed in shallow circular trays, 15 mm by 75 mm in diameter. The swollen RTV model was placed face down in the wet plaster. After the plaster had hardened sufficiently, over a period of 5–10 minutes, the swollen RTV model was removed from the tray and the plaster casting cavity mold was allowed to air dry for 1–2 days.

Example 6

Producing the Powder Compact

A slip mixture of zirconium oxide and water was prepared from 16.00 g zirconium oxide powder (TOSOH Zirconia TZ-3YS powder) and 4.00 g distilled water. After thorough mixing with a plastic spatula, the mixture was allowed to stand for 5 minutes to allow air bubbles to escape. The mold cavities prepared in Example 5, were filled rapidly with the slip mixture and allowed to stand for approximately 5 seconds (this allowed the wall thickness of the cast pieces to reach a satisfactory level), after which time excess slip mixture was removed, using a plastic pipette. The resultant slip castings were left in the mold for approximately ten minutes after which time it was removed from the mold by inverting the mold and rapping it sharply several times. The zirconia slip casting onlays were placed on an alumina insulation block and allowed to air dry for approximately 12 hours.

Example 7

Heating the Zirconia Casting

The castings produced in Example 6, supported on alumina insulation blocks, were placed in a high temperature furnace (Thermolyne High Temperature Furnace—maximum temperature 1700 C.) and fired in an air atmosphere. The heating schedule was as follows:

1. Heat to 500° C., increasing temperature at a rate of 1° C. per minute with no hold at 500° C.

2. Heat from 500° C. to 1500° C. increasing temperature at a rate of 2° C. per minute with a 2-hour hold at 1500° C.

3. Cool to room temperature at a temperature reduction rate of 4° C. per minute.

After the fired castings had cooled, their length and breadth measurements were carefully taken and the ratio of the size of the casting to the original model (coefficient of expansion) determined.

The results of these measurements are set forth below:

| % Tetraglyme (w/w) | % Limonene (w/w) | Degree Enlargement |
|---|---|---|
| 20.0 | 80.0 | 1.022 |
| 27.4 | 72.6 | 0.991 |
| 30.0 | 70.0 | 0.976 |
| 40.0 | 60.0 | 0.928 |
| 60.0 | 40.0 | 0.860 |

The 27.4% (w/w) tetraglyme—72.6% limonene mixture was found to provide nearly exact compensation for the firing shrinkage of the ceramic (coefficient of expansion) of 99.1 %—relative error of 0.9%). These use of other swelling agent mixtures to produce a specific desired enlargement or reduction in the size of the replica in comparison to the original model is shown by the production of ceramic onlays ranging in size from 102.2% to 86.0% of the original model, following the procedure described above. Even more precise control over the degree of enlargement can be achieved by more precise temperature control during immersion in the swelling agent system. Precision calibration of each factor (time, temperature etc) used in the process can provide an even greater level of accuracy.

Following the procedure set forth in the Examples, using the RTV composition of Example 1, in combination with a swelling agent mixture comprised of 27.4% tetraglyme and 72.6% limonene will provide a coefficient of swelling that will equal the coefficient of shrinkage of the ceramic zirconia slip composition used in the above examples. This ratio is easily determined by reference to a graph of the coefficient of swelling plotted as a function of the swelling agent composition in accordance with the procedure disclosed in example 1, above.

By interpolation of a graphical representation of the ratio of swelling using a series of mixtures of tetraglyme and limonene, the variations in the size of the replica which are possible by following the procedure set forth in the examples, ranges from 76% (using no swelling agent) to an estimated 110% (using pure limonene as the swelling agent) of the dimensions of the original onlay model when using the RTV composition of example 1 in conjunction with the ceramic composition of example 5.

Once the coefficient of swelling and the coefficient of shrinkage has been determined for a particular batch of swellable polymer and sinterable composition, it is a simple matter to replicate shaped articles in the manner described above without the need for further testing to determine the coefficient of swelling for the swellable polymer or the coefficient of shrinkage for the slip ceramic composition. For example, all that would be required to make additional replicas of shaped articles using the swellable polymer and the ceramic composition employed in the above examples would be to simply immerse a swellable polymer model produced from the polymer described in Example 1 in the selected swelling agent and thereafter proceeding in the manner described in examples 3 to 7 using the ceramic composition of example 6. Obviously, if it is desired to use either or both, a different swellable polymer or a different ceramic slip composition or if it is desired to alter any of the procedural steps, such as the heating schedule, for example, then the procedures set forth in the Examples using the new materials and/or the different protocol should be repeated.

While the focus of this invention is primarily directed to the accurate replica of shaped articles, it will be appreciated that this invention also permits the production of precise dimensional enlargements as well as scaled reductions in the size of shaped articles. Enlargements are produced utilizing swellable polymers whose coefficient of swelling is greater than the coefficient of shrinkage of the chosen ceramic material. Reductions are possible by producing powder compacts in molds produced from unswollen polymers using slip casting compositions having reproducible coefficients of shrinkage.

What is claimed is:

1. A method for producing a proportionately accurate replica of a shaped article that is equal or greater or smaller in size than said shaped article, which comprises:

a) preparing a replica of said shaped article formed from a swellable polymer, b) immersing said swellable polymer in a swelling agent system at a temperature and for a sufficient period of time to swell said swellable polymer to a predetermined extent in an essentially uniform manner, c) preparing a casting mold from the polymer replica produced in step b) above, d) forming a sinterable powder compact in said casting mold, and e) heating said sinterable powder compact in a selected atmosphere for a predetermined time or times at one or more predetermined temperatures.

2. A method according to claim 1 wherein said swellable polymer is immersed in said swelling agent system for a period of time sufficient to allow said swelling agent system essentially to fully permeate said swellable polymer.

3. A method according to claim 1 wherein said shaped article is a dental restoration in the form of an inlay or an onlay.

4. A method according to claim 1 wherein said swellable polymer is an elastomer.

5. A method according to claim 1 wherein said swellable polymer is a silicone elastomer.

6. A method according to claim 1 wherein said swellable polymer is an RTV silicone polymer.

7. A method according to claim 1 wherein said swelling agent system is an organic liquid that does not react with or dissolve said swellable polymer.

8. A method according to claim 1 wherein said swelling agent system is a combination of two or more organic liquids.

9. A method according to claim 1 wherein said swelling agent system is a mixture of limonene and triglyme or tetraglyme.

10. A method according to claim 1 wherein said sinterable powder compact is comprised of a ceramic powder.

11. A method according to claim 1 wherein said sinterable powder compact is zirconia.

12. A method according to claim 1 wherein said sinterable powder compact is a metal powder.

13. A method for producing a dimensionally accurate solid ceramic replica of a shaped article which comprises:
   a) preparing a replica of a shaped article in the form of a swellable polymer,
   b) immersing said swellable polymer in a swelling agent system at a temperature and for a sufficient period of time to swell said replica to a predetermined extent,
   c) preparing a casting mold from said swelled polymer replica,
   d) forming a sinterable powder compact in said casting mold,
   e) heating said sinterable powder compact for a time or times and at such temperature or temperatures and in such atmosphere as will result in an overall shrinkage of said powder compact as will compensate for the expansion of the swellable polymer replica in step b) above.

14. A method according to claim 13 wherein said shaped article is a dental restoration in the form of an inlay or an onlay.

15. A method according to claim 13 wherein said swellable polymer is an elastomer.

16. A method according to claim 13 wherein said swellable polymer is a silicone elastomer.

17. A method according to claim 13 wherein said swellable polymer is an RTV silicone polymer.

18. A method according to claim 13 wherein said swelling agent system is an organic liquid that does not react with or dissolve said swellable polymer.

19. A method according to claim 13 wherein said swelling agent system is a combination of two or more organic liquids.

20. A method according to claim 13 wherein said swelling agent system is a mixture of limonene and triglyme or tetraglyme.

21. A method according to claim 13 wherein said sinterable powder compact is comprised of a ceramic powder.

22. A method according to claim 13 wherein said sinterable powder compact is zirconia.

23. A method according to claim 13 wherein said sinterable powder compact is a metal powder.

24. A method of producing a dimensionally accurate solid ceramic replica of a shaped article which comprises:
   a) preparing a ceramic powder compact of essentially uniform size and shape,
   b) heating said powder compact in accordance with a predetermined heating schedule comprised of one or more temperatures over one or more periods of time,
   c) comparing the dimensions of said powder compact after heating to the dimensions of said powder compact before heating to determine the Coefficient of Shrinkage of said ceramic powder compact,
   d) preparing a dimensionally accurate replica of a shaped article in the form of a swellable polymer,
   e) swelling said polymer in a swelling agent system selected to result in the expansion of said swellable powder replica to an extent such that a Coefficient results which has the following mathematical relationship to the Coefficient of Shrinkage determined in step c) above:

$$\text{Coefficient of Expansion} = 1/\text{Coefficient of Shrinkage},$$

f) preparing a casting mold from said swelled polymer,
   g) forming a ceramic powder compact in said mold, using the same materials and under essentially the same conditions as were employed in step a) above, and
   h) heating said powder compact using essentially the same heating schedule as was employed in step b) above.

25. In a method of producing a solid ceramic replica of a shaped article by slip casting a ceramic powder compact produced from a casting mold made from an impression of a polymeric replica of a shaped article the improvement which comprises producing said casting mold using a swellable polymer and a ceramic powder compact having a coefficient of expansion and a coefficient of shrinkage, respectively, wherein the mathematical relationship of said coefficients satisfies the following equation:

$$\text{Coefficient of Expansion} = 1/\text{Coefficient of Shrinkage}.$$

26. In a method of producing a solid ceramic replica of a shaped article by heating a ceramic powder compact produced from a casting mold made from an impression of a polymeric replica of a shaped article, the improvement which comprises immersing said polymeric replica in a swelling agent system for a time and at a temperature sufficient to swell said polymeric replica to a predetermined extent which essentially compensates for the shrinkage of said ceramic powder compact when heated, thereby producing a solid ceramic article which essentially is a proportionately and dimensionally accurate replica of said shaped article.

27. In a method of producing a solid ceramic replica of a shaped article by slip casting a ceramic powder compact produced from a casting mold made from an impression of a polymeric replica of a shaped article, the improvement which comprises: producing said ceramic powder compact from a ceramic powder substance having a coefficient of shrinkage having the following mathematical relationship to the Coefficient of Expansion of the polymer used to produce said polymeric replica:

$$\text{Coefficient of Expansion} = 1/\text{Coefficient of Shrinkage}.$$

* * * * *